United States Patent
Fiedler et al.

(10) Patent No.: US 11,208,436 B2
(45) Date of Patent: Dec. 28, 2021

(54) POPULATIONS OF POLYPEPTIDES HAVING A TRIPLE-HELICAL STRUCTURE

(71) Applicant: Navigo Proteins GmbH, Halle/Saale (DE)

(72) Inventors: Erik Fiedler, Halle/Saale (DE); Ulrich Haupts, Halle/Saale (DE); Madlen Zwarg, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 220 days.

(21) Appl. No.: 16/681,058

(22) Filed: Nov. 12, 2019

(65) Prior Publication Data

US 2020/0172580 A1 Jun. 4, 2020

(30) Foreign Application Priority Data

Nov. 12, 2018 (EP) .................................... 18205727

(51) Int. Cl.
    *C07K 14/00* (2006.01)
    *C12N 15/10* (2006.01)
    *G01N 33/543* (2006.01)

(52) U.S. Cl.
    CPC .......... *C07K 14/00* (2013.01); *C12N 15/1037* (2013.01); *G01N 33/54313* (2013.01)

(58) Field of Classification Search
    None
    See application file for complete search history.

(56) References Cited

FOREIGN PATENT DOCUMENTS

| WO | WO 2012/074463 A1 | 6/2012 |
|----|-------------------|--------|
| WO | WO 2014/064092 A1 | 5/2014 |
| WO | WO 2016/005969 A1 | 1/2016 |
| WO | WO 2017/009421 A1 | 1/2017 |
| WO | WO 2018/029157 A1 | 2/2018 |

OTHER PUBLICATIONS

Extended European Search Report corresponding to European Application No. 18 20 5727 dated Jan. 27, 2019.

Hosse et al., "A new generation of protein display scaffolds for molecular recognition," Protein Science, Wiley, vol. 15, No. 1 pp. 14-27 (2006).

*Primary Examiner* — Christopher M Gross
(74) *Attorney, Agent, or Firm* — Jenkins, Wilson, Taylor & Hunt, P.A.

(57) ABSTRACT

Provided are populations of polypeptides, wherein each member of the population of polypeptides includes or is an amino sequence as set forth in SEQ ID NO: 5 or SEQ ID NO: 6. Also provided are methods for identifying polypeptides that bind to pre-selected target molecules, which in some embodiments can include providing a population of polypeptides as described herein, contacting the population of polypeptides with a pre-selected target molecule, and identifying a complex comprising at least one member of the population of polypeptides bound to the pre-selected target molecule; and populations of nucleic acid molecules that encode the presently disclosed populations of polypeptides.

10 Claims, 1 Drawing Sheet

Specification includes a Sequence Listing.

Library "PA11": scaffold randomized in helix 1 and helix 2 (SEQ ID NO: 5)

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|
| I | A | X | F | D | X | A | Q | X | A | X | X | E | I | X | X | L | P | N | L | T | X | E | Q | R | A | F | I | R | X | S | L | X | D | P | S | V | S | L | E | V | L | G | E | A | Q | K | L | N | D | Q | A | P | K |

At positions 7, 10, 14, 17, 18, 24, 28, 32, and 35, X is selected from amino acids H, E, V, A, L, Y, W, K, I, Q, T, and R.
At position 4, X is selected from amino acids L, Y, W, D, K, I, Q, T, and R.
At position 13, X is selected from amino acids H, E, L, Y, W, K, I, Q, and R.

*FIG. 1A*

Library "PA01": scaffold randomized in helix 1 and helix 2 (SEQ ID NO: 6)

| 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|---|---|---|---|---|---|---|---|---|---|
| N | A | X | D | X | A | S | A | X | X | E | I | X | X | L | P | N | L | T | X | X | Q | X | X | X | F | I | X | G | L | X | X | D | P | S | V | S | K | E | V | L | G | E | A | Q | K | L | N | D | S | Q | A | P | K |

X is selected from amino acids A, L, M, F, W, K, Q, E, S, V, I, Y, H, R, D, and T (i.e., amino acids other than C, G, N, P)

*FIG. 1B*

POPULATIONS OF POLYPEPTIDES HAVING A TRIPLE-HELICAL STRUCTURE

CROSS REFERENCE TO RELATED APPLICATION

This application claims the benefit of European Patent Application Ser. No. 18205727.3 filed Nov. 12, 2018, the entire contents of which is incorporated herein by reference.

TECHNICAL FIELD

The presently disclosed subject matter relates in some embodiments to a population of polypeptides having a triple-helical structure. The presently disclosed subject matter further relates in some embodiments to methods for screening the population of polypeptides for specific binding activities, for example, to a target protein. In addition, the presently disclosed subject matter relates in some embodiments to employing the populations of peptides and/or members thereof in a variety of applications in which specific binding to target proteins is important such as but not limited to technical applications including affinity chromatography and in therapy and diagnostics.

BACKGROUND

Libraries of polypeptides provide a great potential for selection of specific target molecules. Such populations of polypeptides comprise numerous potential amino acid sequence combinations and thus provide a high diversity for the selection of binders against a large number of different target molecules. However, there are limitations in experimental options and in success rates of selection procedures.

There is ongoing need for advanced tools that allow an efficient selection of molecules for specific targets as well as the development of new molecules suitable for use in technical applications, therapy and diagnostics.

The presently disclosed subject matter meets this need by providing populations of polypeptides with a triple-helical structure. The novel populations of polypeptides of the presently disclosed subject matter allow the identification of new valuable proteins based on a new concept for the design of polypeptide libraries. The presently disclosed novel library designs with their specific amino acid substitutions clearly provide numerous broadened experimental options and thereby significantly increase the success rate of selection procedures. These populations of polypeptides are particularly advantageous because they allow for the identification of highly selective target-specific molecules that are useful not only in technical applications, but also in therapy and diagnostics.

The above overview is exemplary only and thus does not necessarily describe all of the problems solved by the presently disclosed subject matter.

SUMMARY

This summary lists several embodiments of the presently disclosed subject matter, and in many cases lists variations and permutations of these embodiments.

This summary is merely exemplary of the numerous and varied embodiments.

Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

The present disclosure provides the following [1] to [14], without being specifically limited thereto:

[1] A population of polypeptides having a triple-helical structure and based on amino sequence of SEQ ID NO: 2 or SEQ ID NO: 3 wherein the polypeptide comprises amino acid substitutions in position corresponding to position 4, and optionally position 5, and in helix 1 at positions 7, 10, 13, 14, 17, and 18 of SEQ ID NOs: 2, 3, 5, or 6, and the polypeptides further comprise at least 4 amino acid substitutions at positions selected from amino acids of helix 2, which correspond to positions 24, 25, 27, 28, 29, 32, 35, and 36, of SEQ ID NOs: 2, 3, 5, and 6. In some embodiments, each member of the population of polypeptides comprises, consists essentially of, or consists of an amino acid sequence as set forth in SEQ ID NO: 5 or SED ID NO: 6.

[2] The population of polypeptides of [1] above, wherein each member of the population of polypeptides comprises amino acid substitutions in helix 2 at positions 24, 28, 32, and 35 of SEQ ID NOs: 2, 3, 5, or 6.

[3] The population of polypeptides of [1] or [2] above, wherein each member of the population of polypeptides comprises amino acid substitutions in helix 2 at each of positions 24, 25, 27, 28, 29, 32, 35, and 36 of SEQ ID NOs: 2, 3, 5, or 6.

[4] The population of polypeptides of any one of [1]-[3] above, wherein each member of the population of polypeptides comprises amino acid substitutions in helix 1 at positions 7, 10, 13, 14, 17, and 18 and in helix 2 at one or more of positions 24, 28, 32, and 35 of SEQ ID NO: 2 or SEQ ID NO: 5.

[5] The population of polypeptides of any one of [1]-[4] above, wherein each member of the population of polypeptides comprises one or more amino acid substitutions in helix 1 at positions 7, 10, 13, 14, 17, and 18 and in helix 2 at positions 24, 25, 28, 29, 32, 35, and 36 of SEQ ID NO: 3 or SEQ ID NO: 6.

[6] A population of polypeptides comprising, consisting essentially of, or consisting of the amino sequence IAAX$_4$FDX$_7$AQX$_{10}$AAX$_{13}$X$_{14}$EI X$_{17}$X$_{18}$LPNLTX$_{24}$EQRX$_{28}$AFRX$_{32}$SLX$_{35}$DDPSVSLE-VLGEAQKLNDSQAPK (SEQ ID NO: 5).

[7] A population of polypeptides comprising, consisting essentially of, or consisting of the amino sequence amino sequence NAAX$_4$XDX$_7$AQX$_{10}$SAX$_{13}$X$_{14}$EIX$_{17}$X$_{18}$LPNLTX$_{24}$-X$_{25}$QX$_{27}$X$_{28}$X$_{29}$FIX$_{32}$SLX$_{35}$X$_{36}$DPSVSKEVLGEAQKL-NDSQAPK (SEQ ID NO: 6), wherein X corresponds to any amino acid residue other than Cys, Gly, Asn, and Pro.

[8] The population of polypeptides of any one of [1]-[7] above, wherein the amino acid substitutions and/or each X is independently selected from the group consisting of histidine (H), glutamic acid (E), valine (V), alanine (A), leucine (L), tyrosine (Y), tryptophan (W), lysine (K), isoleucine (I), glutamine (Q), threonine (T), and arginine (R), methionine (M), phenylalanine (F), serine (S), and aspartic acid (D).

[9] The population of polypeptides of [8] above, wherein the amino acid substitutions and/or each X is independently selected from the group consisting of histidine (H), glutamic acid (E), valine (V), alanine (A), leucine (L), tyrosine (Y), tryptophan (W), lysine (K), isoleucine (I), glutamine (Q), threonine (T), and arginine (R).

[10] The population of polypeptides any one of [1]-[9] above, wherein the amino acid in position 4 of any one of SEQ ID NOs: 2, 3, 5, and 6 is selected from the group of leucine (L), tyrosine (Y), tryptophan (W), aspartic acid (D), lysine (K), isoleucine (I), glutamine (Q), threonine (T), and arginine (R) and wherein amino acids in position 13 are selected from histidine (H), glutamic acid (E), leucine (L), tyrosine (Y), tryptophan (W), lysine (K), isoleucine (I), glutamine (Q), and arginine (R).

[11] The population of polypeptides of [1] above, wherein the polypeptide has an alanine (A) in position 8 of any one of SEQ ID NOs: 2, 3, 5, and 6.

[12] A method for generating and/or identifying a polypeptide with binding affinity for a target molecule, the method comprising providing a population of polypeptides according to any one of [1]-[11] above; contacting the population of polypeptides with a target molecule; identifying a complex comprising a member of the population of polypeptides bound to the target molecule; and obtaining the member of the population of polypeptides that is bound to the target molecule, thereby generating and/or identifying a polypeptide with binding affinity to the target molecule. In some embodiments, the binding affinity for the target molecule exceeds a pre-defined minimum.

[13] In some embodiments, the presently disclosed subject matter relates to polypeptides with a binding affinity for a target molecule obtained by the method of [12] above, which in some embodiments is for use in affinity chromatography.

[14] In some embodiments, the presently disclosed subject matter relates to polypeptides with binding affinity for a target molecule obtained by the method of [12] above for use as a medicament, as a diagnostic agent, and/or as a prognostic agent.

It is noted that the Summary presented herein above is non-limiting, and other aspects and embodiments of the presently disclosed subject matter will become evident from the following description, EXAMPLES, and Figures.

BRIEF DESCRIPTION OF THE FIGURES

FIGS. 1A and 1B show structural motifs and amino acid sequences of populations of polypeptides of the presently disclosed subject matter. All library scaffolds are based on randomization in two helical regions (helix 1: amino acids 7-19; helix 2: amino acids 23-37; helix 3: amino acids 40-56). Numbers in the top row refer to the corresponding amino acid position in SEQ ID NOs: 5 and 6. Positions that are randomized are noted with "X". FIG. 1A shows the amino acid sequence of Library PA11 (SEQ ID NO: 5), and FIG. 1B shows the amino acid sequence of Library PA01 (SEQ ID NO: 6). Below each amino acid sequence is a summary of exemplary definitions of X for each library.

DETAILED DESCRIPTION

The novel populations of polypeptides of the presently disclosed subject matter allow for the identification of new valuable proteins based on a new concept for the design of polypeptide libraries. In particular, the libraries as described herein allow for the identification of highly selective, target-specific molecules that are useful not only in technical applications such as affinity chromatography, but also in therapy and diagnostics.

Disclosed herein are solutions needs in the art based on engineering polypeptide libraries designed around artificial triple helix proteins. In particular, polypeptides with three-helix bundles are employed as scaffolds for the libraries with amino acid variabilities at specific selected amino acid positions. The amino acid positions which are randomized in the respective libraries have been selected based on their orientation towards one side of the triple helical structures. The total number of randomized amino acids can be in some embodiments between 11 and 16, and can be expected to allow for sufficient interactions at their surfaces with a pre-determined target molecule (e.g., a protein) to provide low to high affinity binding while still preserving the basic triple-helical structure and stability of the library (e.g., scaffold) polypeptide. The novel library designs disclosed herein with the specific amino acid substitutions identified by the present inventors clearly provide broadened experimental options and can increase the success rate of selection strategies designed to identify binding partners. This allows for the generation of a broad set of new target-specific binding molecules, each of which is characterized by having a three-helix structure.

Before the presently disclosed subject matter is described in more detail below, it is to be understood that the presently disclosed subject matter is not limited to the particular methodology, protocols, and reagents described herein as these may vary. It is also to be understood that the terminology used herein is for the purpose of describing particular aspects and embodiments only, and is not intended to limit the scope of the presently disclosed subject matter as reflected in the appended claims.

In some embodiments, the terms used herein are defined as described in "A multilingual glossary of biotechnological terms: (IUPAC Recommendations)", Leuenberger et al. eds. (1995), Helvetica Chimica Acta, CH-4010 Basel, Switzerland).

Several documents (for example: patents, patent applications, scientific publications, manufacturer's specifications, instructions, GENBANK® Accession Number sequence submissions, etc.) may be cited throughout the present application. Nothing herein is to be construed as an admission that the presently disclosed subject matter is not entitled to antedate such disclosure by virtue of prior invention. Some of the documents cited herein may be characterized as being "incorporated by reference". In the event of a conflict between the definitions or teachings of such incorporated references and definitions or teachings recited in the present application, the text of the present application takes precedence.

All sequences referred to herein are disclosed in the attached sequence listing that, with its whole content and disclosure, forms part of the disclosure content of the present application.

I. Definitions

Unless defined otherwise, all technical and scientific terms used herein have the same meaning as commonly understood by one of ordinary skill in the art to which this invention belongs. This includes a skilled person working in the field of protein engineering and purification, but also including a skilled person working in the field of developing new target-specific binding molecules for use in technical applications and in therapy and diagnostics.

Throughout this specification and the claims, which follow, unless the context requires otherwise, the word "comprise", and grammatical variants thereof such as but not limited to "comprises" and "comprising", will be understood to imply the inclusion of a recited element or step, or group of elements or steps, but not the exclusion of any other element or step or group of elements or steps. The term "comprise(s)" or "comprising" may encompass a limitation to "consists of" or "consisting of", should such a limitation be necessary for any reason and to any extent.

Thus, the term "comprising", which is synonymous with "including" "containing", or "characterized by", is inclusive or open-ended and does not exclude additional, unrecited elements and/or method steps. "Comprising" is a term of art that means that the named elements and/or steps are present, but that other elements and/or steps can be added and still fall within the scope of the relevant subject matter.

As used herein, the phrase "consisting of" excludes any element, step, or ingredient not specifically recited. It is noted that, when the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of the related disclosure or claim to the specified materials and/or steps, plus those that do not materially affect the basic and novel characteristic(s) of the disclosed and/or claimed subject matter. For example, a pharmaceutical composition can "consist essentially of" a pharmaceutically active agent or a plurality of pharmaceutically active agents, which means that the recited pharmaceutically active agent(s) is/are the only pharmaceutically active agent(s) present in the pharmaceutical composition. It is noted, however, that carriers, excipients, and/or other inactive agents can and likely would be present in such a pharmaceutical composition, and are encompassed within the nature of the phrase "consisting essentially of".

With respect to the terms "comprising", "consisting of", and "consisting essentially of", where one of these three terms is used herein, the presently disclosed and claimed subject matter can include the use of either of the other two terms. For example, in some embodiments, the presently disclosed subject matter relates to compositions comprising antibodies. It would be understood by one of ordinary skill in the art after review of the instant disclosure that the presently disclosed subject matter thus encompasses compositions that consist essentially of the antibodies of the presently disclosed subject matter, as well as compositions that consist of the antibodies of the presently disclosed subject matter.

The terms "protein" and "polypeptide" refer to any chain of two or more amino acids linked by peptide bonds, and does not refer to a specific length of the product. Thus, "peptides", "protein", "amino acid chain", or any other term used to refer to a chain of two or more amino acids, are included within the definition of "polypeptide", and the term "polypeptide" may be used instead of, or interchangeably with, any of these terms. The term "polypeptide" is also intended to refer to the products of post-translational modifications of the polypeptide, which are well known in the art.

The terms "triple-helical structure" or "three-helix structure" refer to a polypeptide with three-helix bundles, wherein the polypeptide comprises in some embodiments at least 48 amino acids, in some embodiments at least 58 amino acids, with helix 1 corresponding to amino acid residues 7-19, helix 2 corresponding to amino acid residues 23-37, and helix 3 corresponding to amino acid residues 40-56 of any one of SEQ ID NOs: 1-6. Accordingly, a polypeptide of the presently disclosed subject matter comprises in some embodiments three helices, with helix 1 corresponding to amino acid residues 7-19 of SEQ ID NO: 2, 3, 5, or 6; helix 2 corresponding to amino acid residues 23-37 of SEQ ID NO: 2, 3, 5, or 6; and helix 3 corresponding to amino acid residues 40-56 of SEQ ID NO: 2, 3, 5, or 6. Further disclosed herein are embodiments of the polypeptide having a triple-helical structure provided by the presently disclosed subject matter, wherein helix 1 with respect to its positions corresponds essentially to positions 6-19 of the amino acid sequence of SEQ ID NO: 2, 3, 5, or 6; helix 2 with respect to its positions corresponds essentially to positions 23-37 of the amino acid sequence of SEQ ID NO: 2, 3, 5, or 6; and helix 3 with respect to its positions corresponds essentially to positions 40-56 of the amino acid sequence of SEQ ID NO: 2, 3, 5, or 6.

The term "modification" or "amino acid modification" refers to a substitution, a deletion, or an insertion of a reference amino acid at a particular position in a parent polypeptide sequence by another amino acid. Given the known genetic code in view of recombinant and synthetic DNA techniques, one of ordinary skill in the art can readily construct DNAs encoding the amino acid variants of the presently disclosed subject matter.

The terms "variant" or "derivative" as used herein includes an amino acid sequence that differs from another reference amino acid sequence by at least one amino acid substitution, deletion, and/or insertion. The term "variant" according to the presently disclosed subject matter refers to a polypeptide based on SEQ ID NO: 2, 3, 5, or 6 having in some embodiments a maximum of 20 amino acid substitutions as compared to SEQ ID NO: 2 or SEQ ID NO: 3. A variant according to the presently disclosed subject matter is characterized by a triple-helix motif as defined herein. In some embodiments, a variant of the polypeptide of SEQ ID NO: 2 or SEQ ID NO: 3 may encompass a deletion of up to 6 amino acid residues at the N-terminus, and/or up to 4 amino acid residues at the C-terminus relative to the amino acid sequence of SEQ ID NO: 2 or SEQ ID NO: 3.

The terms "population" and "library" may be used interchangeably herein. A library may be a population of polypeptides or of polynucleotides. In other words, the library may take the form of a population or mixture or plurality of polypeptides or nucleic acids. A library may be a collection of variants.

A "randomly modified nucleotide or amino acid sequence" is a nucleotide or amino acid sequence which in a number of positions has been subjected to substitution, insertion, and/or deletion by nucleotides or amino acids.

The term "target" or "target protein" as used herein refers to a protein or peptide or fragments thereof and the like having an antigen or epitope recognized by a variant protein of the presently disclosed subject matter.

The terms "binding affinity" and "binding activity" may be used herein interchangeably, and they refer to the ability of a polypeptide of the presently disclosed subject matter to bind to another protein, peptide, and/or fragment and/or domain thereof. Binding affinity is typically measured and reported by the equilibrium dissociation constant ($K_D$), which is used to evaluate and rank order strengths of bimolecular interactions. The lower the $K_D$ value, the greater the binding affinity of the biomolecule for its binding partner. The higher the $K_D$ value, the more weakly the binding partners bind to each other. The binding affinity and dissociation constants can be measured quantitatively by, e.g., surface plasmon resonance (SPR). Other methods for determining binding affinities are well known to the skilled person and can be selected, for instance, from the following: enzyme-linked immunosorbent assay (ELISA), kinetic exclusion analysis (KinExA assay), Bio-layer interferometry (BLI), flow cytometry, fluorescence spectroscopy techniques, isothermal titration calorimetry (ITC), analytical ultracentrifugation, radioimmunoassay (RIA or IRMA), and enhanced chemiluminescence (ECL). Typically, a dissociation constant $K_D$ is determined at 20° C., 25° C., or 30° C. If not specifically indicated otherwise, the $K_D$ values recited herein are determined at 25° C. by surface plasmon resonance (SPR).

The terms "target" and "target protein" refer to a protein, peptide, and the like having an antigen or epitope recognized by at least one of the variant proteins of the presently disclosed subject matter.

The term "amino acid sequence identity" refers to a quantitative comparison of the identity (or differences) of the amino acid sequences of two or more proteins. "Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity. To determine the sequence identity, the sequence of a query protein is aligned to the sequence of a reference protein or polypeptide, for example, to the polypeptide of SEQ ID NO: 2 or SEQ ID NO: 3. Methods for sequence alignment are well known in the art. For example, for determining the extent of an amino acid sequence identity of an arbitrary polypeptide relative to the amino acid sequence of, for example, SEQ ID NO: 2 or SEQ ID NO: 3, the SIM Local similarity program is preferably employed (Huang & Webb Miller (1991) A time-efficient, linear-space local similarity algorithm. Advances in Applied Mathematics 12:337-357), that is freely available. For multiple alignment analysis, ClustalW can be used (Thompson et al. (1994) Nucleic Acids Res 22:4673-4680).

II. Exemplary Embodiments

Structural Characterization by Substitutions in SEQ ID NO: 2 or SEQ ID NO: 3 in Defined Positions of Helix 1 and Helix 2.

A population of polypeptides as disclosed herein is characterized in having at least 6 amino acids substituted in the first helix of a parental protein (e.g., SEQ ID NO: 2 or SEQ ID NO: 3) in defined positions and in having at least 4 amino acids substituted in the second helix of a parental protein with triple-helical structure (e.g., SEQ ID NO: 2 or SEQ ID NO: 3). It is noted that SEQ ID NO: 2 and SEQ ID NO: 3 are the amino acid sequences of alkaline-stable parental proteins with triple helical structure for the generation of the populations of alkaline stable polypeptides of the presently disclosed subject matter. The populations of polypeptides are exemplified by SEQ ID NO: 5 and SEQ ID NO: 6. Positions for randomization are shown in FIGS. 1A and 1B.

In some embodiments, the presently disclosed subject matter relates to populations of polypeptides having a triple-helical structure and derived from amino sequence of a parental proteins with triple-helical structure (e.g., SEQ ID NO: 2 or SEQ ID NO: 3) wherein the polypeptide comprises amino acid substitutions in position corresponding to position 4, and optionally position 5, and further in helix 1 at positions 7, 10, 13, 14, 17, and 18 of SEQ ID NO: 2 or SEQ ID NO: 3. The populations of polypeptides as disclosed herein are further characterized structurally in that they further comprise at least 4 amino acid substitutions in helix 2 at positions 24, 25, 27, 28, 29, 32, 35, and 36 of SEQ ID NO: 2 or SEQ ID NO: 3.

A population of polypeptides as disclosed herein is structurally further characterized in that it comprises amino acid substitutions in helix 2 at positions 24, 28, 32, and 35 of SEQ ID NO: 2 or SEQ ID NO: 3, in addition to substitutions in helix 1 at positions 7, 10, 13, 14, 17, and 18 of SEQ ID NO: 2 or SEQ ID NO: 3.

In some embodiments, the presently disclosed populations of polypeptides are structurally further characterized in that the comprise amino acid substitutions in helix 2 at positions 24, 25, 27, 28, 29, 32, 35, and 36 of SEQ ID NO: 2 or SEQ ID NO: 3, in addition to substitutions in helix 1 at positions 7, 10, 13, 14, 17, and 18 of SEQ ID NO: 2 or SEQ ID NO: 3.

In some embodiments, a population of polypeptides as disclosed herein is structurally further characterized in that it comprises amino acid substitutions at position 4 and position 5, and in helix 1 at positions 7, 10, 13, 14, 17, and 18 and in helix 2 at positions 24, 28, 32, and 35 of SEQ ID NO: 2. An exemplary such library comprises, consists essentially of, or consists of an amino acid sequence as set forth in SEQ ID NO: 5.

In some embodiments, a population of polypeptides as disclosed herein is structurally further characterized in that it the polypeptide comprises amino acid substitutions at position 4, and in helix 1 at positions 7, 10, 13, 14, 17, and 18 and in helix 2 at positions 24, 25, 28, 29, 32, 35, and 36 of SEQ ID NO: 3. An exemplary such library comprises, consists essentially of, or consists of an amino acid sequence as set forth in SEQ ID NO: 6.

In some embodiments, at least 4 amino acids are randomized in at least one helix in order to generate a unique and specific novel binding affinity. In some embodiments, at least 6 amino acids are randomized in helix 1 and at least 4 amino acids are randomized in helix 2 in order to generate a unique and specific novel binding affinity of a triple helix monomeric protein of 58 amino acids to a target protein.

Non-limiting exemplary substitutions of the amino acid sequences of SEQ ID NOs: 2 and 3 are as follows. In some embodiments, a population of polypeptides as disclosed herein is structurally further characterized in that the amino acid in each position X of SEQ ID NO: 5 or SEQ ID NO: 6 is independently selected from any of the 20 naturally occurring amino acids other than cysteine (C), glycine (G), asparagine (N), and proline (P). In some embodiments, a population of polypeptides as disclosed herein is structurally further characterized in that the amino acid in each position X of SEQ ID NO: 5 or SEQ ID NO: 6 is independently selected from the group consisting of histidine (H), glutamic acid (E), valine (V), alanine (A), leucine (L), tyrosine (Y), tryptophan (W), lysine (K), isoleucine (I), glutamine (Q), threonine (T), and arginine (R), methionine (M), phenylalanine (F), serine (S), and aspartic acid (D).

In some embodiments, a population of polypeptides as disclosed herein is structurally further characterized in that the amino acid in each position X of SEQ ID NO: 5 or SEQ ID NO: 6 is selected from the group consisting of histidine (H), glutamic acid (E), valine (V), alanine (A), leucine (L), tyrosine (Y), tryptophan (W), lysine (K), isoleucine (I), glutamine (Q), threonine (T), and arginine (R).

In some embodiments, a population of polypeptides as disclosed herein is structurally further characterized in that the amino acid in position 4 of SEQ ID NO: 5 or SEQ ID NO: 6 is selected from the group consisting of leucine (L), tyrosine (Y), tryptophan (W), aspartic acid (D), lysine (K), isoleucine (I), glutamine (Q), threonine (T), and arginine (R).

In some embodiments, a population of polypeptides as disclosed herein is structurally further characterized in that the amino acid in position 13 of SEQ ID NO: 5 or SEQ ID NO: 6 is selected from the group consisting of histidine (H), glutamic acid (E), leucine (L), tyrosine (Y), tryptophan (W), lysine (K), isoleucine (I), glutamine (Q), and arginine (R).

In some embodiments, a population of polypeptides as disclosed herein is structurally further characterized in that polypeptides have an alanine (A) in position 8 of SEQ ID NO: 5 or SEQ ID NO: 6.

In some embodiments, a population of polypeptides as disclosed herein is structurally further characterized in having at least 70% sequence identity to an amino acid sequence of SEQ ID NO: 2 or SEQ ID NO: 3. Exemplary randomized positions and exemplary combinations of amino acid positions for substitutions and non-limiting embodiments of the presently disclosed polypeptides are shown in FIGS. 1A and 1B.

Structural Characterization by Positions that are not Mutated.

In some embodiments, a polypeptide as disclosed herein is structurally characterized in that certain residues in helix 1 or helix 2 are not subject to substitution, in particular the amino acid residues at the positions corresponding to positions 8, 9, 12, 15, 16, 19, 23, 26, 30, 33, 34, and 37 of SEQ ID NO: 5 or SEQ ID NO: 6. Thus, in some embodiments, a polypeptide as disclosed herein is structurally characterized in that the amino acid residues at the positions corresponding to positions 8, 9, 12, 15, 16, 19, 23, 26, 30, 33, 34, and/or 37 of SEQ ID NO: 5 or SEQ ID NO: 6 are as follows: the amino acid residue at the position corresponding to position 8 is alanine (A), the amino acid residue at the position corresponding to position 9 is glutamine (Q), the amino acid residue at the position corresponding to position 12 is alanine (A), the amino acid residue at the position corresponding to position 15 is glutamic acid (E), the amino acid residue at the position corresponding to position 16 is isoleucine (I), the amino acid residue at the position corresponding to position 19 is leucine (L), the amino acid residue at the position corresponding to position 23 is threonine (T), the amino acid residue at the position corresponding to position 26 is glutamine (Q), the amino acid residue at the position corresponding to position 32 is serine (S), the amino acid residue at the position corresponding to position 30 is phenylalanine (F), the amino acid residue at the position corresponding to position 34 is leucine (L), and the amino acid residue at the position corresponding to position 37 is aspartic acid (D).

Polypeptides with Triple-Helical Structure; Library Scaffolds. Randomization in Helix 1 and Adjacent Amino Acids and in Helix 2 (Library PA11; FIG. 1A).

The presently disclosed subject matter furthermore provides populations of polypeptides that in some embodiments comprise, consist essentially of, or consist of a triple-helical structure and comprising the amino acid sequence IAAX$_4$FDX$_7$AQX$_{10}$AAX$_{13}$X$_{14}$EIX$_{17}$X$_{18}$LPNLTX$_{24}$EQ-RX$_{28}$AFRX$_{32}$SLX$_{35}$DDPSVSLEVLG EAQKLNDSQAPK (SEQ ID NO: 5), wherein X$_7$, X$_{10}$, X$_{14}$, X$_{17}$, X$_{18}$, X$_{24}$, X$_{28}$, X$_{32}$, and X$_{35}$ are each individually any of histidine (H), glutamic acid (E), valine (V), alanine (A), leucine (L), tyrosine (Y), tryptophan (W), lysine (K), isoleucine (I), glutamine (Q), threonine (T), and arginine (R), and X$_4$ is any of leucine (L), tyrosine (Y), tryptophan (W), aspartic acid (D), lysine (K), isoleucine (I), glutamine (Q), threonine (T), and arginine (R); and X$_{13}$ is any of histidine (H), glutamic acid (E), leucine (L), tyrosine (Y), tryptophan (W), lysine (K), isoleucine (I), glutamine (Q), and arginine (R).

Randomization in Helix 1 and Adjacent Amino Acids and in Helix 2 (Library PA01; FIG. 1B).

The presently disclosed subject matter also provides populations of polypeptides having a triple-helical structure and comprising the amino acid sequence NAAX$_4$X$_5$DX$_7$AQX$_{10}$SAX$_{13}$X$_{14}$EIX$_{17}$X$_{18}$LPNLTX$_{24}$-X$_{25}$QX$_{27}$X$_{28}$X$_{29}$FIX$_{32}$SLX$_{35}$X$_{36}$DPSVSKEVLGEAQK-LNDSQAPK (SEQ ID NO: 6), wherein X$_4$, X$_5$, X$_7$, X$_{10}$, X$_{13}$, X$_{14}$, X$_{17}$, X$_{18}$, X$_{24}$, X$_{25}$, X$_{27}$, X$_{28}$, X$_{29}$, X$_{32}$, X$_{35}$, and X$_{36}$, are each individually any of alanine (A), leucine (L), methionine (M), phenylalanine (F), tryptophan (W), lysine (K), glutamine (Q), glutamic acid (E), serine (S), valine (V), isoleucine (I), tyrosine (Y), histidine (H), arginine (R), aspartic acid (D), and threonine (T), thereby excluding cysteine (C), glycine (G), asparagine (N), and proline (P) from each of these enumerated amino acid positions.

Population of Polypeptides.

The presently disclosed subject matter further provides in some embodiments populations and/or libraries of the polypeptides of the presently disclosed subject matter as disclosed herein. The population of polypeptides provided by the presently disclosed subject matter comprises novel artificial polypeptides having a triple-helical structure and having at least 70% sequence identity to the amino sequence of a parental protein as defined in SEQ ID NO: 2 or SEQ ID NO: 3 (e.g., derivatives of artificial alkaline stable triple helical proteins as designated herein as SEQ ID NO: 2 or SEQ ID NO: 3, wherein the polypeptides are structurally characterized according to the aspects and embodiments described elsewhere herein).

Identity of Polypeptides in Populations to Parental Scaffold.

In some embodiments, a polypeptide of the presently disclosed subject matter as disclosed herein has a triple-helical structure and in some embodiments may have at least 70% sequence identity to an amino sequence as set forth in SEQ ID NO: 2 or SEQ ID NO: 3. A polypeptide of the presently disclosed subject matter has a triple-helical structure and may have in some embodiments at least 71%, in some embodiments at least 72%, in some embodiments at least 73%, in some embodiments at least 74%, in some embodiments at least 75%, in some embodiments at least 76%, in some embodiments at least 77%, in some embodiments at least 78%, and in some embodiments at least 79% or more sequence identity to the amino sequence of the corresponding parental protein (SEQ ID NO: 2 or SEQ ID NO: 3). In some embodiments, a polypeptide of the presently disclosed subject matter comprises, consists essentially of, or consists of an amino acid sequence as set forth in SEQ ID NO: 5 or SEQ ID NO: 6.

In some embodiments, a polypeptide of the presently disclosed subject matter and as present in the presently disclosed populations of proteins has a triple-helical structure and may have at least 80% sequence identity to the amino sequence of alkaline stable SEQ ID NO: 2 or SEQ ID NO: 3. A polypeptide as disclosed herein can have a triple-helical structure and may have in some embodiments at least 81%, in some embodiments at least 82%, in some embodiments at least 83%, in some embodiments at least 84%, in some embodiments at least 85%, in some embodiments at least 86%, in some embodiments at least 87%, in some embodiments at least 88%, and in some embodiments at least 89% or more sequence identity to the amino sequence of the corresponding parental protein (SEQ ID NO: 2 or SEQ ID NO: 3). In some embodiments, a polypeptide of the presently disclosed subject matter comprises, consists essentially of, or consists of an amino acid sequence as set forth in SEQ ID NO: 5 or SEQ ID NO: 6.

In some embodiments, variants may have any amino acid identity between 70% identity and 90% identity, which in some embodiments can be 80% to 85% identity, and in some embodiments about 81% identity, to the amino acid sequence of alkaline stable, non-Fc binding protein of SEQ ID NO: 2 (PAdelFc). In some embodiments, variants of the presently disclosed subject matter may have an amino acid identity between 70% identity and 90% identity, which in some embodiments can be 70% to 75% identity, and in some embodiments about 72% identity, to the amino acid sequence of alkaline stable, Fc binding protein of SEQ ID NO: 3 (C27). Variants of SEQ ID NO: 3 show no detectable or reduced Fc binding.

Methods for Selecting from a Library.

In some embodiments, the presently disclosed subject matter relates to methods for selecting from a library comprising variants of the scaffold of parental protein SEQ ID NO: 2 or SEQ ID NO: 3, one or more of said variants having a specific binding affinity to a target protein or target peptide, said method comprising providing a library of polypeptides of SEQ ID NO: 5 and/or SEQ ID NO: 6; contacting the library with the target protein under conditions and for a time sufficient to permit one or more polypeptides of SEQ ID NO: 5 or SEQ ID NO: 6 and the target protein or peptide to interact; and selecting and/or otherwise identifying from the library one or more polypeptides of SEQ ID NO: 5 or SEQ ID NO: 6 having a pre-selected specific binding affinity ($K_D$) to the target protein that exceeds a minimum. In some embodiments, the pre-selected specific binding affinity ($K_D$) to the target protein is in a range of $10^{-5}$ to $10^{-12}$ M.

Method for Producing a Library of the Presently Disclosed Subject Matter.

In addition to the libraries described elsewhere herein, the presently disclosed subject matter provides methods for producing such libraries as disclosed herein with randomized amino acid positions, as shown by the sequences of FIGS. 1A and 1B. The presently disclosed subject matter thus in some embodiments encompasses libraries of SEQ ID NO: 5 or SEQ ID NO: 6 as shown in FIGS. 1A and 1B produced by the presently disclosed methods.

As a state-of-the-art method for library synthesis the favorable triplet technology (Morphosys Slonomics) is capable of synthesizing random libraries with an even (or if desired, uneven) distribution of, for example the 20 natural amino acids. Assuming a random distribution of the 20 natural amino acids at, for example 7 to 16 positions, this generates a pool of $20^7$ to $20^{16}$ theoretical derivatives of SEQ ID NO: 2 or SEQ ID NO: 3 (e.g., as shown in SEQ ID NO: 5 or SEQ ID NO: 6, respectively). In some embodiments, the amino acids Cysteine (C), Glycine, Asparagine (N), and Proline (P) are excluded at all of the randomized positions, resulting in $16^7$ to $16^{16}$ theoretical derivatives of SEQ ID NO: 2 or SEQ ID NO: 3. This large pool of polypeptides constitutes a library of different derivatives of SEQ ID NO: 2 and SEQ ID NO: 3, and is shown in SEQ ID NO: 5 and SEQ ID NO: 6, respectively.

The polypeptide libraries of the presently disclosed subject matter can be produced by generating mutagenized nucleic acid molecules encoding the same comprising randomized nucleotide triplets encoding positions in, in some embodiments, helix 1 and helix 2 of SEQ ID NO: 2 or SEQ ID NO: 3 as described herein above and in FIGS. 1A and 1B, thereby resulting in one or more nucleic acid molecules which encode and can be employed to express the one or more nucleic acid molecules in a suitable expression system.

In some embodiments, the presently disclosed subject matter relates to libraries comprising a plurality of the non-naturally occurring derivatives of SEQ ID NO: 2 or SEQ ID NO: 3 as described herein and as shown in SEQ ID NO: 5 or SEQ ID NO: 6. The libraries provided herein may comprise, for example, a sequence diversity of polypeptides, each member of which comprises a different amino acid sequence. Sequence differences between library members are responsible for the diversity present in the library. In some embodiments, of the presently disclosed subject matter, a nucleic acid library is provided encoding derivatives of SEQ ID NO: 2 or SEQ ID NO: 3, wherein the amino acid residues as described in FIGS. 1A and 1B are substituted by any amino acid except C, G, N, P. Advantageously, the nucleic acids are in some embodiments incorporated into expression vectors to allow production of the polypeptides encoded by the nucleic acids in host cells and/or expression systems.

Library Display.

A library of the presently disclosed subject matter may be displayed on the surfaces of ribosomes, bacteriophage, viruses, bacteria, yeast cells, or any other appropriate host cell, and can be subjected to repeated rounds of panning against the respective target. Contacting according to the presently disclosed subject matter is in some embodiments performed via a suitable presentation and selection method such as the phage display, ribosomal display, mRNA display or cell surface display, yeast surface display, or bacterial surface display methods. The methods mentioned above are known to those skilled in the art.

In the phage display procedure described herein, recombinant derivatives of SEQ ID NO: 2 or SEQ ID NO: 3 as exemplified in FIGS. 1A and 1B are expressed on the surface of a filamentous phage while the coding DNA of the presented variation is present at the same time packed in a single-stranded form in the phage envelope. Thus, in the frame of an affinity enrichment variations having certain properties can be selected from a library and their genetic information can be amplified by infection of suitable bacteria or added to another cycle of enrichment, respectively. Presentation of derivatives of SEQ ID NO: 2 or SEQ ID NO: 3 on the phage surface can be achieved, for example, by genetic fusion to a signal sequence and a capsid or surface protein of the phage. Furthermore, the encoded proteins can be designed to include further functional elements such as but not limited to one or more affinity tags and/or antibody epitopes for detection and/or purification by affinity chromatography, and/or protease recognition sequence(s) for specific cleavage of the protein in the course of the affinity enrichment.

The genetic vector suitable for the selection procedure in the context of the isolation of derivatives of SEQ ID NO: 2 or SEQ ID NO: 3 and into which the gene cassette for the fusion protein described is inserted is referred to as phagemid. Among others, it contains the intergenic region of a filamentous phage (e.g. M13 or f1) or a portion thereof which in the case of a superinfection of the bacterial cell carrying the phagemid by means of helper phages results in the packaging of a covalently closed strand of phagemid DNA into a phage capsid.

Phage particles obtained can be selected with respect to the binding of the derivatives of SEQ ID NO: 2 or SEQ ID NO: 3 presented thereon to any target by means of methods known to those skilled in the art. For this purpose, the presented derivatives of SEQ ID NO: 2 or SEQ ID NO: 3 can be transiently immobilized to target protein and can be specifically eluted after non-binding variations have been separated. The phage particles obtained in this manner can be re-amplified and enriched by successive cycles of selection and amplification of derivatives of SEQ ID NO: 2 or SEQ ID NO: 3 with binding properties to selected targets.

Isolation of Variants.

Derivatives of parental proteins SEQ ID NO: 2 or SEQ ID NO: 3, as shown in SEQ ID NO: 5 or SEQ ID NO: 6 (see FIGS. 1A and 1B) from enriched phage pools are cloned into expression vectors for individual protein expression. In some embodiments, expression of the derivatives of SEQ ID NO: 2 or SEQ ID NO: 3 as shown in FIGS. 1A and 1B enables screening for specific binding proteins by established techniques, such as ELISA on automated high-throughput screening platforms. Identified clones with desired binding properties can then be sequenced to reveal the amino acid sequences. The identified protein may be subjected to further maturation steps, for example, by generating additional libraries based on alterations of the identified sequences and repeated phage display, ribosomal display, panning and screening steps as described above. The expressed proteins can be contacted with a target protein to enable binding of the partners to each other. This process enables identification (selection) of those proteins which have a binding activity to the given target protein. The present invention permits the person skilled in the art to enrich a chosen repertoire of derivatives of SEQ ID NO: 2 or SEQ ID NO: 3, which are functional (e.g. non-Fc binding, stable) and capable of binding to a given target (except IgG).

Method of Generation of a Novel Polypeptide.

The presently disclosed subject matter further provides in some embodiments methods for generating novel polypeptides as disclosed herein with binding affinities for target proteins (e.g., pre-selected target proteins). In some embodiments, the methods comprise (i) providing one or more novel polypeptides as disclosed herein, or a population of novel polypeptides as disclosed herein; (ii) contacting the one or more polypeptides of (i), or the population (library) of polypeptides of (i), with a target protein; (iii) identifying a complex comprising a novel polypeptide as disclosed herein bound to the target protein; and (iv) obtaining a novel polypeptide disclosed herein which is capable of binding to the target protein. In some embodiments, a novel polypeptide obtained by the methods described herein is capable of binding to the target protein with specific affinity in the range between $10^{-5}$ to $10^{-12}$ M, in some embodiments with a high affinity in the nanomolar range (e.g., a $K_D$ in the range between $10^{-7}$ to $10^{-9}$ M). A novel polypeptide obtained by the methods disclosed herein, which is capable of binding to the target protein (with high affinity), can be used in technical applications such as affinity chromatography, in diagnostics, and/or in therapy. Such aspects are encompassed by the presently disclosed subject matter. In some embodiments, a novel polypeptide obtained by the methods disclosed herein is capable of binding to the target protein.

A presently disclosed method for generating a novel polypeptide with binding affinity for a target protein may further comprise determining the binding affinity of the polypeptide to the target protein. The binding affinity may be determined by any appropriate technique such as, but not limited to those described herein.

Some embodiments of the presently disclosed subject matter relate to methods for generating a variant protein derived from the polypeptide of SEQ ID NO: 2 or SEQ ID NO: 3, said methods comprising (i) subjecting nucleotide triplets of a nucleic acid molecule encoding the amino acid sequence of the polypeptide of SEQ ID NO: 2 or SEQ ID NO: 3 to mutagenesis; (ii) obtaining one or more variant nucleic acid molecule(s); (iii) expressing the one or more variant nucleic acid molecule(s) obtained in (ii) in a suitable expression system; and (iv) enriching the one or more variant proteins by means of selection and/or isolation, wherein the variant protein has at least 70% sequence identity to the amino acid sequence of SEQ ID NO: 2 or SEQ ID NO: 3. The mutagenesis takes into account any of the structural technical features according to the aspects and embodiments described elsewhere herein in relation to the novel polypeptides of the present invention.

Uses of the Novel Polypeptides in Technical Applications (e.g. Affinity Chromatography).

Also provided herein are uses of a novel polypeptide of the presently disclosed subject matter, including novel polypeptides having binding affinity for a target protein obtained by the herein-described methods, in technical applications such as, but not limited to affinity chromatography.

As described herein, affinity chromatography (also called affinity purification) makes use of specific binding interactions between molecules. For example, the novel polypeptides derived from parental amino acid sequences SEQ ID NO: 2 or SEQ ID NO: 3 as described herein, and/or polypeptides generated and/or obtained by any of the methods as described herein, are in some embodiments immobilized as ligand to a solid support so that when a complex mixture is passed over the solid support, those target proteins having specific binding affinity to a protein of the presently disclosed subject matter become bound to the protein of the presently disclosed subject matter. After other sample components are washed away, the bound target protein is stripped from the support, resulting in its purification from the original sample. Methods for immobilization of protein and methods for affinity chromatography are well known in the field of protein engineering and purification, and can easily performed by a skilled person in this field using standard techniques and equipment.

The presently disclosed subject matter further provides in some embodiments methods for affinity purifying target proteins, in particular a target protein or a domain or fragment of said target protein. In some embodiments, the methods comprise (a) providing a liquid containing a target protein; (b) providing an affinity separation matrix with immobilized polypeptides obtained by the above-described methods; (c) contacting said liquid with said affinity separation matrix, wherein said target protein binds to a immobilized polypeptides obtained by the above-described methods; and (d) eluting the target protein from said matrix, which in some embodiments can be accomplished by a change in pH and/or a change in salt concentration, thereby obtaining an eluate containing the target protein in a purified form. In some embodiments, the presently disclosed affinity purification methods may further comprise one or more washing steps carried out under conditions sufficient to remove from the affinity separation matrix some or all molecules that are non-specifically bound thereto. Affinity separation matrixes suitable for the disclosed uses and methods are those matrixes according to the aspects and embodiments described above, and as known to a person skilled in the art.

Compositions.

Further provided herein are compositions comprising polypeptides with binding activities for target proteins obtained by the herein-described methods. In some embodiments, such compositions can comprise a diagnostically and/or therapeutically effective dose or amount of a novel polypeptide of the presently disclosed subject matter. The amount of protein to be administered can depend, inter alia, on the organism to be treated, the type of disease, the age and weight of the patient, and/or other factors.

In some embodiments, a composition of the presently disclosed subject matter is a diagnostic composition comprising a polypeptide of the presently disclosed subject matter and a diagnostically acceptable carrier. In some embodiments, the composition is a pharmaceutical composition comprising a polypeptide of the presently disclosed subject matter and a pharmaceutically acceptable carrier. The compositions optionally can contain further auxiliary agents and excipients known to the one of ordinary skill in the art. By way of example and not limitation, these can include stabilizing agents, surface-active agents, salts, buffers, coloring agents, etc.

Compositions comprising at least one polypeptide of the presently disclosed subject matter can be prepared by methods known in the art. For example, the type of pharmaceutical preparation may depend on the particular type of disease to be treated, the route of administration, the severity of the disease, the patient to be treated, and/or other factors known to those skilled in the art of medicine.

Still further provided herein is the use of polypeptides with binding activity for a target protein obtained by the herein-described methods, or the use of the herein-described compositions, as medicaments, diagnostic agents, and/or prognostic agents.

EXAMPLES

The following EXAMPLES are provided for further illustration of the presently disclosed subject matter. The presently disclosed subject matter, however, is not limited thereto, and the following EXAMPLES merely show the practicability of the presently disclosed subject matter on the basis of the above description. For a complete disclosure of the presently disclosed subject matter, reference is made also to the literature cited in the application which is incorporated completely into the application by reference.

Example 1

Library Construction and Cloning

Scaffold libraries comprising randomized amino acid positions in triple helical proteins were synthesized by triplet technology (ThermoFisher Scientific—GeneArt, Germany) or in house by randomized oligonucleotides generated by synthetic trinucleotide phosphoramidites (ELLA Biotech) to achieve a well-balanced amino acid distribution with simultaneously exclusion of cysteine and other amino acid residues at randomized positions. The scaffolds for the libraries are shown as SEQ ID NO: 2 and SEQ ID NO: 3 (see Table 1). The scaffolds have 58 amino acids and a triple-helical structure. The scaffolds may differ in a maximum of 5 positions selected from the group of 1N or 1I, 11S or 11A, 31R or 31I, and 42K or 42L. SEQ ID NO: 2 shows no binding to IgG Fc domains. In Table 1, underlined are amino acid residues 7-19 (helix 1), amino acid residues 23-37 (helix 2), and amino acid residues 40-56 (helix 3).

TABLE 1

| Parental Proteins with Triple Helix Structure |
|---|
| SEQ ID NO: 2 (PAdelFc) | IAAKFD<u>EAQSAADSEILHL</u>PNL<u>TEEQRNAFRQSLSDD</u> PS<u>VSLEVLGEAQKLNDSQAPK</u> |
| SEQ ID NO: 3 (C27) | NAAKFD<u>EAQQSAFYEILHL</u>PNL<u>TEEQRNAFIQSLKDD</u> PS<u>VSKEVLGEAQKLNDSQAPK</u> |

SEQ ID NO: 2 was randomized in 6 amino acid positions in helix 1, and in position 4, and in 4 positions in helix 2, as illustrated in FIG. 1A. A total of 11 amino acids were randomized. SEQ ID NO: 5 shows the non-Fc binding protein PAdelFc (SEQ ID NO: 2) with randomized positions (PA11 library).

SEQ ID NO: 3 was randomized in 6 amino acid positions in helix 1, and in position 4 and 5, and in 8 positions in helix 2, as illustrated in FIG. 1B. A total of 16 amino acids were randomized. SEQ ID NO: 6 shows the alkaline stable protein C27 (SEQ ID NO: 3) with randomized positions (PA01 library).

Amino acids allowed for randomization at each position are indicated in FIGS. 1A and 1B.

The corresponding cDNA library for PA01 (FIG. 1B) was provided by ThermoFisher Scientific as GeneArt Strings DNA Fragments. The coding region comprising helices 2-3 was amplified by PCR. Full length library molecules were generated by overlap extension PCR (oePCR), in which non-randomized regions (helix 3) were amplified using C27 as template sequence.

Cloning of PA11 (FIG. 1A) was performed using randomized oligonucleotides (ELLA Biotech). The PAdelFc sequence served as template. Full length PA11 was generated by oePCR of one fragment comprising randomized helix 1 and another fragment comprising helix 3 and randomized helix 2.

All generated library PCR products were ligated with a modified pCD87SA phagemid (herein referred to as pCD33-OmpA) using standard methods known to a skilled person. The pCD33-OmpA phagemid comprises an OmpA leader sequence and a direct fusion to CT-pIII. Aliquots of the ligation mixture were used for electroporation of *Escherichia coli* SS320 (Lucigen). Established recombinant genetic methods as known to somebody skilled in the art and as described in more detail in Settele et al. (2018) Construction and Selection of AFFILIN® Phage Display Libraries. In: Hust & Lim (eds) *Phage Display. Methods in Molecular Biology*, vol 1701. Humana Press, New York, were used.

Example 2

Primary Selection by TAT Phage Display

The naïve library was enriched against the target using phage display as selection system. After transformation of competent bacterial SS320 cells (Lucigene) with phagemid pCD33-OmpA carrying the library, phage amplification and purification was carried out using standard methods known to a skilled person. For selection the target protein was immobilized as Fc-fusion of the target on DYNABEADS® Protein A or DYNABEADS® Protein G. The target concentration during phage incubation was lowered from 200 nM (first round) to 100 nM (second round) and 50 nM (third round). Target phage complexes were magnetically separated from supernatant and washed several times. Target bound phages were eluted by trypsin. To deplete the phage library of Fc-binding variants a preselection of phages with immobilized Fc-fragment of $IgG_1$ (Athens Research & Technology) was performed prior to round two and three. To identify target specific phage pools, eluted and reamplified phages of each selection round were analyzed by phage pool ELISA. Wells of a medium binding microtiter plate (Greiner Bio-One) were coated with TARGET-Fc (2.5 µg/ml) and Fc-fragment of IgG1 (2.5 µg/ml), respectively. Bound phages were detected using α-M13 HRP-conjugated antibody (GE Healthcare).

Example 3

Cloning of Target Binding Phage Pools into an Expression Vector

Selection pools showing specific binding to the target in phage pool ELISA were amplified by PCR according to methods known in the art, cut with appropriate restriction nucleases and ligated into a derivative of the expression vector pET-28a (Merck, Germany) comprising a Strep-Tag II (IBA GmbH).

Example 4

Single Colony Hit Analysis

After transformation of BL21 (DE3) cells (Merck, Germany) kanamycin-resistant single colonies were grown. Expression of the target-binding modified scaffold variants was achieved by cultivation in 384 well plates (Greiner Bio-One) using auto induction medium (Studier (2005) Protein Expr. Purif 41(1):207-234). Cells were harvested and subsequently lysed chemically or enzymatically by BugBuster reagent (Novagen) and mechanically by freeze/thaw cycles, respectively. After centrifugation the resulting supernatants were screened by ELISA with immobilized target on High Bind 384 ELISA microtiter plates (Greiner Bio-One). Detection of bound protein was achieved by STREP-TACTIN® HRP Conjugate (IBA GmbH) in combination with TMB-Plus Substrate (Biotrend, Germany). The reaction was stopped by addition of 0.2 M $H_2SO_4$ solution and measured in a plate reader at 450 nm versus 620 nm.

Example 5

Maturation Selection and Analysis

For affinity maturation two rounds of panning were performed. Fc-fusion of target was employed at a concentration of 50 nM and 5 nM in round one and two, respectively. For both rounds a preselection with Fc-fragment of $IgG_1$ was performed. To analyze the matured and selected pools for specific target binding a phage pool ELISA was performed followed by cloning of positive pools into expression vector pET-28a and hit ELISA as described above.

Example 6

Expression and Purification of Proteins

Proteins were cloned to an expression vector using standard methods known to a skilled person, purified and analyzed as described below.

All constructs were expressed in *Escherichia coli* BL21 (DE3) using a low copy plasmid system under regulation of a T7 promoter. Proteins were produced cytoplasmatically in soluble form after induction by lactose included in the medium (autoinduction medium). All overnight cultures were inoculated from a single colony after a fresh transformation with a defined plasmid.

Bacterial cultures for the production of proteins were incubated in the RAMbio system. Overnight cultures were grown up to saturation in baffled shake flasks in a volume of 100 mL in 2×YT medium (1% yeast extract, 1.7% casein, 0.5% NaCl, 1% glucose supplemented with 50 μg/mL kanamycin). Main cultures were inoculated to an optical density (OD600) of 0.5 and grown in 350 mL modified H15 medium (2% glucose, 0.89% glycerol, 0.76% lactose, 5% yeast extract, 250 mM MOPS, 202 mM Tris supplemented with 50 μg/mL kanamycin and 0.014% (v/v) SE15 (antifoam, 10%)) for up to 24 h at 37° C. Harvested biomass was stored at −20° C. upon further purification steps were initialized.

Proteins with affinity tag were purified by affinity chromatography and size exclusion. After affinity chromatography purification a size exclusion chromatography (SE HPLC or SEC) has been performed using an Akta system and a SUPERDEX™ 200 HiLoad 16/600 column (GE Healthcare). The SEC column has a volume of 120 ml and was equilibrated with 2 CV. The samples were applied with a flow rate of 1 ml/min. Fraction collection starts as the signal intensity reaches 10 mAU. Following SDS-PAGE analysis positive fractions were pooled and their protein concentrations were measured.

Proteins without affinity tag were purified by SP-Sepharose HP (GE Healthcare) followed by anion exchange chromatography (Q Sepharose HP, GE Healthcare). Finally, a size exclusion chromatography (Sephacryl S200HR, GE Healthcare) was performed. Further analysis included SDS-PAGE, SE-HPLC and RP-HPLC. Protein concentrations were determined by absorbance measurement at 280 nm using the molar absorbent coefficient. Reversed phase chromatography (RP-HPLC) has been performed using a Dionex HPLC system and a PLRP-S (5 μm, 300 Å) column (Agilents).

Example 7

Analysis of Proteins by Surface Plasmon Resonance (SPR)

The $IgG_1$-Fc-domain was immobilized on a CM-5 sensor chip (GE Healthcare); the chip was equilibrated with SPR running buffer. Surface-exposed carboxylic groups were activated by passing a mixture of EDC and NHS to yield reactive ester groups. 700-1500 RU target (on-ligand) were immobilized on a flow cell, IgG-Fc (off-ligand) was immobilized on another flow cell. Injection of ethanolamine after ligand immobilization was used to block unreacted NHS groups. Upon ligand binding, protein analyte was accumulated on the surface increasing the refractive index. This change in the refractive index was measured in real time and plotted as response or resonance units (RU) versus time. The analytes were applied to the chip in serial dilutions with a flow rate of 30 μl/min. The association was performed for 120 seconds and the dissociation for 360 seconds. After each run, the chip surface was regenerated with 30 μl regeneration buffer (10 mM HCL) and equilibrated with running buffer. A dilution series served as positive control, whereas a dilution series of unmodified scaffold represents the negative control. The control samples were applied to the matrix with a flow rate of 30 μl/min, while they associate for 60 seconds and dissociate for 120 seconds. Regeneration and re-equilibration were performed as previously mentioned. Binding studies were carried out by the use of the BIAcore 3000 (GE Healthcare); data evaluation was operated via the BIAevaluation 3.0 software, provided by the manufacturer, by the use of the Langmuir 1:1 model (RI=0). Evaluated dissociation constants ($K_D$) were standardized against off-target and indicated.

What is claimed is:

1. A population of polypeptides, wherein each member of the population of polypeptides comprises, consists essentially of, or consists of an amino sequence selected from the group consisting of:

(a)
(SEQ ID NO: 5)

$IAAX_4FDX_7AQX_{10}AAX_{13}X_{14}EIX_{17}X_{18}LPNLTX_{24}EQRX_{28}AFRX_{32}SLX_{35}DD$

PSVSLEVLGEAQKLNDSQAPK;
and (b)
(SEQ ID NO: 6)

$NAAX_4XDX_7AQX_{10}SAX_{13}X_{14}EIX_{17}X_{18}LPNLTX_{24}X_{25}QX_{27}X_{28}X_{29}FIX_{32}SL$ $X_{35}X_{36}$DPSVSKEVLGEAQKLNDSQAPK, and further wherein each X is independently selected from the group consisting of aspartic acid (D), glutamic acid (E), lysine (K), arginine (R), histidine (H), tyrosine (Y), glutamine (Q), serine (S), threonine (T), alanine (A), valine (V), leucine (L), isoleucine (I), methionine (M), phenylalanine (F), and tryptophan (W).

2. The population of polypeptides of claim 1, wherein each X is independently selected from the group consisting of histidine (H), glutamic acid (E), valine (V), alanine (A), leucine (L), tyrosine (Y), tryptophan (W), lysine (K), isoleucine (I), glutamine (Q), threonine (T), and arginine (R).

3. The population of polypeptides of claim 1, wherein $X_4$ of each member of the population of polypeptides is selected from the group of leucine (L), tyrosine (Y), tryptophan (W), aspartic acid (D), lysine (K), isoleucine (I), glutamine (Q), threonine (T), and arginine (R).

4. The population of polypeptides of claim 1, wherein $X_{13}$ of each member of the population of polypeptides is selected from the group consisting of histidine (H), glutamic acid (E), leucine (L), tyrosine (Y), tryptophan (W), lysine (K), isoleucine (I), glutamine (Q), and arginine (R).

5. The population of polypeptides of claim 1, wherein each member of the population of polypeptides comprises the amino sequence $IAAX_4FDX_7AQX_{10}AAX_{13}X_{14}EIX_{17}X_{18}LPNLTX_{24}EQRX_{28}AFRX_{32}SLX_{35}D$-DPSVSL EVLGEAQKLNDSQAPK (SEQ ID NO: 5), and further wherein:

(i) $X_7$, $X_{10}$, $X_{14}$, $X_{17}$, $X_{18}$, $X_{24}$, $X_{28}$, $X_{32}$, and $X_{35}$ are independently selected from the group consisting of A, E, H, I, L, K, Q, R, T, V, W, and Y;

(ii) $X_4$ is selected from the group consisting of D, I, K, L, Q, R, T, W, and Y; and (iii) $X_{13}$ is selected from the group consisting of E, H, I, K, L, Q, R, W, and Y.

6. The population of polypeptides of claim 1, wherein each member of the population of polypeptides comprises an amino sequence $NAAX_4XDX_7AQX_{10}SAX_{13}X_{14}EIX_{17}X_{18}LPNLTX_{24}X_{25}QX_{27}X_{28}X_{29}FIX_{32}SLX_{35}X_{36}D$ PSVSKEVLGEAQKLNDSQAPK (SEQ ID NO: 6), and further wherein each X is independently selected from the group consisting of aspartic acid (D), glutamic acid (E), lysine (K), arginine (R), histidine (H), tyrosine (Y), glutamine (Q), serine (S), threonine (T), alanine (A), valine (V), leucine (L), isoleucine (I), methionine (M), phenylalanine (F), and tryptophan (W).

7. The population of polypeptides of claim 1, wherein each member of the population is attached to a solid support.

8. The population of polypeptides of claim 7, wherein the solid support is selected from the group consisting of plastic, glass, ceramic, silicone, metal, cellulose and a particle.

9. The population of polypeptides of claim 8, wherein the solid support is in a form selected from the group consisting of a membrane, a gel, a magnetic particle, and a bead.

10. A method for identifying a polypeptide that binds to a pre-selected target molecule, the method comprising providing the population of polypeptides according to claim 1, contacting the population of polypeptides with a pre-selected target molecule, and identifying a complex comprising at least one member of the population of polypeptides bound to the pre-selected target molecule.

* * * * *

SEQUENCE LISTING

<160> NUMBER OF SEQ ID NOS: 8

<210> SEQ ID NO 1
<211> LENGTH: 58
<212> TYPE: PRT
<213> ORGANISM: Artificial Sequence
<220> FEATURE:
<223> OTHER INFORMATION: PA05 artifical scaffold sequence for library

<400> SEQUENCE: 1

```
Ile Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Arg Gln
            20                  25                  30

Ser Leu Ser Asp Asp Pro Ser Val Ser Leu Glu Val Leu Gly Glu Ala
        35                  40                  45

Gln Lys Leu Asn Asp Ser Gln Ala Pro Lys
    50                  55
```

<210> SEQ ID NO 2
<211> LENGTH: 53
<212> TYPE: PRT
<213> ORGANISM: Artificial Sequence
<220> FEATURE:
<223> OTHER INFORMATION: PA11 artifical sequence for library

<400> SEQUENCE: 2

```
Ile Ala Ala Lys Phe Asp Glu Ala Gln Ser Ala Ala Asp Ser Glu Ile
1               5                   10                  15

Leu His Leu Pro Asn Leu Thr Glu Glu Gln Arg Asn Ala Phe Arg Gln
            20                  25                  30

Ser Leu Ser Asp Asp Pro Ser Val Ser Leu Glu Val Leu Gly Glu Ala
        35                  40                  45

Gln Lys Leu Asn Asp
    50
```

<210> SEQ ID NO 3
<211> LENGTH: 58
<212> TYPE: PRT
<213> ORGANISM: Artificial Sequence
<220> FEATURE:
<223> OTHER INFORMATION: PA01 artifical scaffold sequence for library

<400> SEQUENCE: 3

```
Asn Ala Ala Lys Phe Asp Glu Ala Gln Gln Ser Ala Phe Tyr Glu Ile
1               5                   10                  15

Leu His Leu Pro Asn Leu Thr Glu Glu Gln Arg Asn Ala Phe Ile Gln
            20                  25                  30

Ser Leu Lys Asp Asp Pro Ser Val Ser Lys Glu Val Leu Gly Glu Ala
        35                  40                  45

Gln Lys Leu Asn Asp Ser Gln Ala Pro Lys
    50                  55
```

<210> SEQ ID NO 4
<211> LENGTH: 58
<212> TYPE: PRT
<213> ORGANISM: Artificial Sequence
<220> FEATURE:
<223> OTHER INFORMATION: PA05 library
<220> FEATURE:
<221> NAME/KEY: Xaa
<222> LOCATION: (4)..(4)
<223> OTHER INFORMATION: X can be any amino acid except C, G, N, or P

```
<220> FEATURE:
<221> NAME/KEY: Xaa
<222> LOCATION: (5)..(5)
<223> OTHER INFORMATION: X can be any amino acid except C, G, N, or P
<220> FEATURE:
<221> NAME/KEY: Xaa
<222> LOCATION: (7)..(7)
<223> OTHER INFORMATION: X can be any amino acid except C, G, N, or P
<220> FEATURE:
<221> NAME/KEY: Xaa
<222> LOCATION: (10)..(10)
<223> OTHER INFORMATION: X can be any amino acid except C, G, N, or P
<220> FEATURE:
<221> NAME/KEY: Xaa
<222> LOCATION: (13)..(13)
<223> OTHER INFORMATION: X can be any amino acid except C, G, N, or P
<220> FEATURE:
<221> NAME/KEY: Xaa
<222> LOCATION: (14)..(14)
<223> OTHER INFORMATION: X can be any amino acid except C, G, N, or P
<220> FEATURE:
<221> NAME/KEY: Xaa
<222> LOCATION: (17)..(17)
<223> OTHER INFORMATION: X can be any amino acid except C, G, N, or P
<220> FEATURE:
<221> NAME/KEY: Xaa
<222> LOCATION: (18)..(18)
<223> OTHER INFORMATION: X can be any amino acid except C, G, N, or P

<400> SEQUENCE: 4

Ile Ala Ala Xaa Xaa Asp Xaa Ala Gln Xaa Ser Ala Xaa Xaa Glu Ile
1               5                   10                  15

Xaa Xaa Leu Pro Asn Leu Thr Glu Glu Gln Arg Asn Ala Phe Arg Gln
            20                  25                  30

Ser Leu Ser Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 5
<211> LENGTH: 58
<212> TYPE: PRT
<213> ORGANISM: Artificial Sequence
<220> FEATURE:
<223> OTHER INFORMATION: PA11 library
<220> FEATURE:
<221> NAME/KEY: Xaa
<222> LOCATION: (4)..(4)
<223> OTHER INFORMATION: can be any amino acid selected from L, Y, W, D,
      K, I, Q, T, R
<220> FEATURE:
<221> NAME/KEY: Xaa
<222> LOCATION: (7)..(7)
<223> OTHER INFORMATION: can be selected from H, E, V, A, L, Y, W, K, I,
      Q, T, R
<220> FEATURE:
<221> NAME/KEY: Xaa
<222> LOCATION: (10)..(10)
<223> OTHER INFORMATION: can be selected from H, E, V, A, L, Y, W, K, I,
      Q, T, R
<220> FEATURE:
<221> NAME/KEY: Xaa
<222> LOCATION: (13)..(13)
<223> OTHER INFORMATION: can be selected from H, E, L, Y, W, K, I, Q, R
<220> FEATURE:
<221> NAME/KEY: Xaa
<222> LOCATION: (14)..(14)
<223> OTHER INFORMATION: can be selected from H, E, V, A, L, Y, W, K, I,
      Q, T, R
<220> FEATURE:
<221> NAME/KEY: Xaa
<222> LOCATION: (17)..(17)
<223> OTHER INFORMATION: can be selected from H, E, V, A, L, Y, W, K, I,
      Q, T, R
```

```
<220> FEATURE:
<221> NAME/KEY: Xaa
<222> LOCATION: (18)..(18)
<223> OTHER INFORMATION: can be selected from H, E, V, A, L, Y, W, K, I,
      Q, T, R
<220> FEATURE:
<221> NAME/KEY: Xaa
<222> LOCATION: (24)..(24)
<223> OTHER INFORMATION: can be selected from H, E, V, A, L, Y, W, K, I,
      Q, T, R
<220> FEATURE:
<221> NAME/KEY: Xaa
<222> LOCATION: (28)..(28)
<223> OTHER INFORMATION: can be selected from H, E, V, A, L, Y, W, K, I,
      Q, T, R
<220> FEATURE:
<221> NAME/KEY: Xaa
<222> LOCATION: (32)..(32)
<223> OTHER INFORMATION: can be selected from H, E, V, A, L, Y, W, K, I,
      Q, T, R
<220> FEATURE:
<221> NAME/KEY: Xaa
<222> LOCATION: (35)..(35)
<223> OTHER INFORMATION: can be selected from H, E, V, A, L, Y, W, K, I,
      Q, T, R

<400> SEQUENCE: 5

Ile Ala Ala Xaa Phe Asp Xaa Ala Gln Xaa Ala Ala Xaa Xaa Glu Ile
1               5                   10                  15

Xaa Xaa Leu Pro Asn Leu Thr Xaa Glu Gln Arg Xaa Ala Phe Arg Xaa
            20                  25                  30

Ser Leu Xaa Asp Asp Pro Ser Val Ser Leu Glu Val Leu Gly Glu Ala
        35                  40                  45

Gln Lys Leu Asn Asp Ser Gln Ala Pro Lys
    50                  55

<210> SEQ ID NO 6
<211> LENGTH: 58
<212> TYPE: PRT
<213> ORGANISM: Artificial Sequence
<220> FEATURE:
<223> OTHER INFORMATION: PA01 library
<220> FEATURE:
<221> NAME/KEY: Xaa
<222> LOCATION: (4)..(4)
<223> OTHER INFORMATION: X can be any amino acid except C, G, N, or P
<220> FEATURE:
<221> NAME/KEY: Xaa
<222> LOCATION: (5)..(5)
<223> OTHER INFORMATION: X can be any amino acid except C, G, N, or P
<220> FEATURE:
<221> NAME/KEY: Xaa
<222> LOCATION: (7)..(7)
<223> OTHER INFORMATION: X can be any amino acid except C, G, N, or P
<220> FEATURE:
<221> NAME/KEY: Xaa
<222> LOCATION: (10)..(10)
<223> OTHER INFORMATION: X can be any amino acid except C, G, N, or P
<220> FEATURE:
<221> NAME/KEY: Xaa
<222> LOCATION: (13)..(13)
<223> OTHER INFORMATION: X can be any amino acid except C, G, N, or P
<220> FEATURE:
<221> NAME/KEY: Xaa
<222> LOCATION: (14)..(14)
<223> OTHER INFORMATION: X can be any amino acid except C, G, N, or P
<220> FEATURE:
<221> NAME/KEY: Xaa
<222> LOCATION: (17)..(17)
<223> OTHER INFORMATION: X can be any amino acid except C, G, N, or P
<220> FEATURE:
<221> NAME/KEY: Xaa
<222> LOCATION: (18)..(18)
<223> OTHER INFORMATION: X can be any amino acid except C, G, N, or P
```

```
<220> FEATURE:
<221> NAME/KEY: Xaa
<222> LOCATION: (24)..(24)
<223> OTHER INFORMATION: X can be any amino acid except C, G, N, or P
<220> FEATURE:
<221> NAME/KEY: Xaa
<222> LOCATION: (25)..(25)
<223> OTHER INFORMATION: X can be any amino acid except C, G, N, or P
<220> FEATURE:
<221> NAME/KEY: Xaa
<222> LOCATION: (27)..(27)
<223> OTHER INFORMATION: X can be any amino acid except C, G, N, or P
<220> FEATURE:
<221> NAME/KEY: Xaa
<222> LOCATION: (28)..(28)
<223> OTHER INFORMATION: X can be any amino acid except C, G, N, or P
<220> FEATURE:
<221> NAME/KEY: Xaa
<222> LOCATION: (29)..(29)
<223> OTHER INFORMATION: X can be any amino acid except C, G, N, or P
<220> FEATURE:
<221> NAME/KEY: Xaa
<222> LOCATION: (32)..(32)
<223> OTHER INFORMATION: X can be any amino acid except C, G, N, or P
<220> FEATURE:
<221> NAME/KEY: Xaa
<222> LOCATION: (35)..(35)
<223> OTHER INFORMATION: X can be any amino acid except C, G, N, or P
<220> FEATURE:
<221> NAME/KEY: Xaa
<222> LOCATION: (36)..(36)
<223> OTHER INFORMATION: X can be any amino acid except C, G, N, or P

<400> SEQUENCE: 6

Asn Ala Ala Xaa Xaa Asp Xaa Ala Gln Xaa Ser Ala Xaa Xaa Glu Ile
1               5                   10                  15

Xaa Xaa Leu Pro Asn Leu Thr Xaa Xaa Gln Xaa Xaa Xaa Phe Ile Xaa
            20                  25                  30

Ser Leu Xaa Xaa Asp Pro Ser Val Ser Lys Glu Val Leu Gly Glu Ala
            35                  40                  45

Gln Lys Leu Asn Asp Ser Gln Ala Pro Lys
    50                  55

<210> SEQ ID NO 7
<211> LENGTH: 58
<212> TYPE: PRT
<213> ORGANISM: Artificial Sequence
<220> FEATURE:
<223> OTHER INFORMATION: PA01 example for a binding protein

<400> SEQUENCE: 7

Asn Ala Ala Val Thr Asp Lys Ala Gln Glu Ser Ala Trp Asp Glu Ile
1               5                   10                  15

Gln Met Leu Pro Asn Leu Thr Thr Glu Gln Ile Trp Arg Phe Ile Val
            20                  25                  30

Ser Leu Lys Glu Asp Pro Ser Val Ser Lys Glu Val Leu Gly Glu Ala
            35                  40                  45

Gln Lys Leu Asn Asp Ser Gln Ala Pro Lys
    50                  55

<210> SEQ ID NO 8
<211> LENGTH: 58
<212> TYPE: PRT
<213> ORGANISM: Artificial Sequence
<220> FEATURE:
<223> OTHER INFORMATION: PA01 example for a binding protein

<400> SEQUENCE: 8
```

-continued

```
Asn Ala Ala Thr Gln Asp Asp Ala Gln Phe Ser Ala Ile Asp Glu Ile
1               5                   10                  15

Gln Ser Leu Pro Asn Leu Thr Val Glu Gln Ile Trp Gln Phe Ile Val
            20                  25                  30

Ser Leu Arg Thr Asp Pro Ser Val Ser Lys Glu Val Leu Gly Glu Ala
        35                  40                  45

Gln Lys Leu Asn Asp Ser Gln Ala Pro Lys
    50                  55
```